United States Patent [19]

Barbaro

[11] Patent Number: 4,790,670
[45] Date of Patent: Dec. 13, 1988

[54] BAG WITH CLOSEABLE FLAP AND METHOD OF MANUFACTURING SAME

[75] Inventor: Matthew Barbaro, Kings Park, N.Y.

[73] Assignee: Poly-Pak Industries, Inc., Melville, N.Y.

[21] Appl. No.: 690,676

[22] Filed: Jan. 11, 1985

[51] Int. Cl.$^4$ .............................................. B65D 33/16
[52] U.S. Cl. ...................................... 383/62; 206/632; 383/10; 383/14; 383/85; 383/86.2; 493/189
[58] Field of Search ..................... 383/9, 62, 119, 84, 383/86, 10, 17, 14, 27, 85, 86.2; 493/189; 206/632

[56] References Cited

U.S. PATENT DOCUMENTS

| | | |
|---|---|---|
| 21,714 | 2/1841 | Rambold . |
| 353,692 | 12/1886 | Magee . |
| 1,128,192 | 2/1915 | Smith ........................ 383/62 |
| 1,288,290 | 12/1918 | Thrasher ..................... 383/84 |
| 1,341,834 | 6/1920 | Nelson et al. . |
| 1,817,868 | 8/1931 | Bauman . |
| 2,211,556 | 8/1940 | Brell et al. . |
| 2,401,109 | 5/1946 | Rohdin . |
| 2,668,769 | 2/1954 | Schlienz . |
| 2,709,467 | 5/1955 | Hoeppner . |
| 2,837,268 | 6/1958 | Potdevin et al. . |
| 2,861,735 | 11/1958 | Faltin .................. 383/84 X |
| 3,024,962 | 3/1962 | Meister ............... 383/119 X |
| 3,204,760 | 9/1965 | Whiteford . |
| 3,235,168 | 2/1966 | Nichols . |
| 3,248,040 | 4/1966 | Friedman . |
| 3,255,951 | 6/1966 | Chan ........................ 383/10 |
| 3,281,056 | 10/1966 | Kugler . |
| 3,363,828 | 1/1968 | Foglia et al. . |
| 3,365,116 | 1/1968 | Ludlow . |
| 3,420,433 | 1/1969 | Bostwick . |
| 3,429,498 | 2/1969 | Dorfman . |
| 3,439,867 | 4/1969 | Paxton . |
| 3,456,867 | 7/1969 | Repko . |
| 3,462,070 | 8/1969 | Corella . |
| 3,519,197 | 7/1970 | Campbell . |
| 3,552,638 | 1/1971 | Quackenbush . |
| 3,570,751 | 3/1971 | Trewella . |
| 3,608,709 | 9/1971 | Pike ...................... 206/631 X |
| 3,613,874 | 10/1971 | Miller . |
| 3,623,653 | 11/1971 | Work . |
| 3,655,503 | 4/1972 | Stanley et al. . |
| 3,693,867 | 9/1972 | Schwarzkopf . |
| 3,761,013 | 9/1973 | Schuster ................... 206/632 X |
| 3,910,488 | 10/1975 | Goodrich . |
| 3,942,713 | 3/1976 | Olson et al. . |
| 3,958,749 | 5/1976 | Goodrich . |
| 3,980,223 | 9/1976 | Curran . |
| 4,015,771 | 4/1977 | Sengewald . |

(List continued on next page.)

FOREIGN PATENT DOCUMENTS

| | | | |
|---|---|---|---|
| 1951142 | 4/1971 | Fed. Rep. of Germany | ........ 383/10 |
| 98571 | 7/1961 | Netherlands . | |
| 0098571 | 7/1961 | Netherlands | ............ 383/86 |

*Primary Examiner*—Stephen Marcus
*Assistant Examiner*—Bryon Gehman
*Attorney, Agent, or Firm*—Lerner, David, Littenberg, Krumholz & Mentlik

[57] ABSTRACT

A bag having a closeable flap portion, and a method of manufacturing same, are disclosed. The bag includes first and second panel portions, and a top flap portion extending from and integral to the second panel portion along a fold line adjacent to an opening between the first and second panel portions. The inner surfaces of the first and second panel portions have surface characteristics rendering them capable of being firmly heat sealed together along the side edges thereof, while the outer surfaces of at least the second panel portion and of the flap portion along the side edges have surface characteristics rendering them capable of only being weakly heat sealed together. The flap portion is initially folded onto the outer surface of the second panel portion and is held thereinplace along the side edges by means of a weakened seam achieved by virtue of heat sealing of the side edges of the first and second panel portions and the flap portion. The end of the flap portion remote from the fold line is adapted to be pulled away from the outer surface of the second panel portion to break the weakened seal between the flap portion and the second panel portion while maintaining the integrity of the side edge seams along the inner surfaces of the first and second panel portions.

20 Claims, 3 Drawing Sheets

U.S. PATENT DOCUMENTS 4,088,264   5/1978   Vogt.
4,102,487   7/1978   Soto.
4,108,351   8/1978   Hough.
4,117,934   10/1978  Mowli et al.
4,189,050   2/1980   Jensen et al.
4,192,448   3/1980   Porth.
4,211,267   7/1980   Skovgaard.
4,243,171   1/1981   Prin .................................. 383/10 X
4,264,392   4/1981   Watt ................................ 206/631 X
4,276,982   7/1981   Sibrava.
4,394,955   7/1983   Raines et al.
4,402,403   9/1983   Focke et al.
4,410,130   10/1983  Herrington.
4,417,659   11/1983  Hatchell.

U.S. Patent   Dec. 13, 1988   Sheet 1 of 3   4,790,670
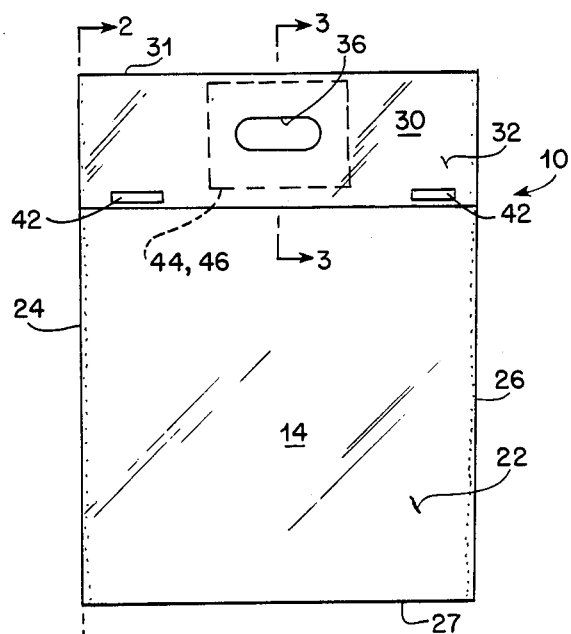
FIG. 1
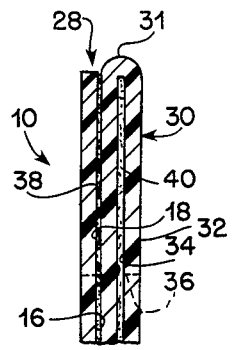
FIG. 2
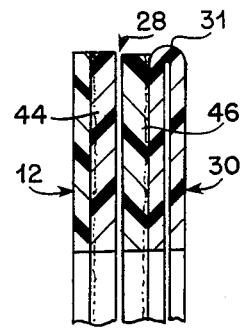
FIG. 3
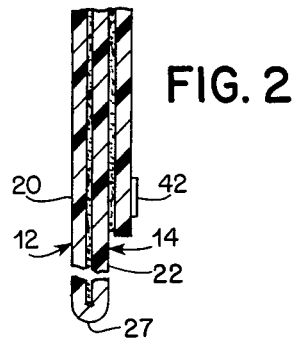

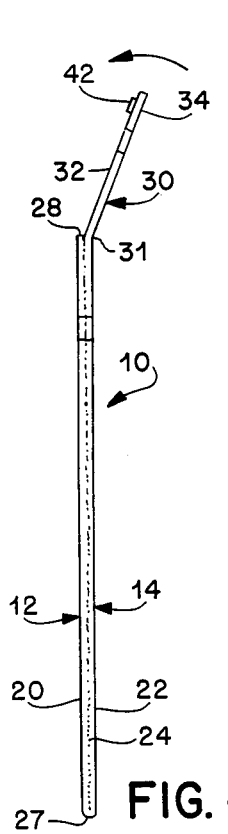
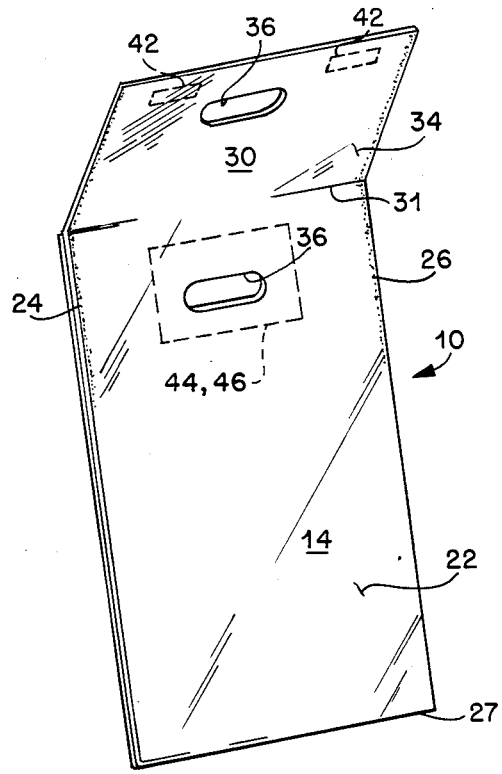
FIG. 4  FIG. 5
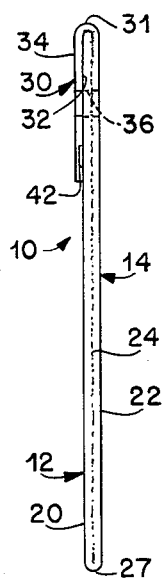
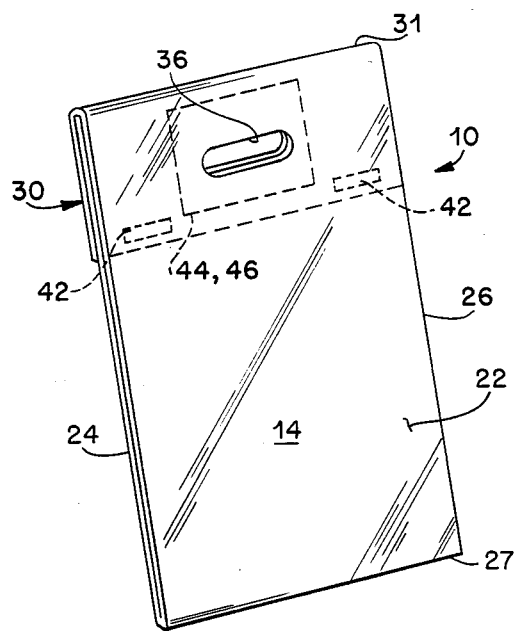
FIG. 6  FIG. 7

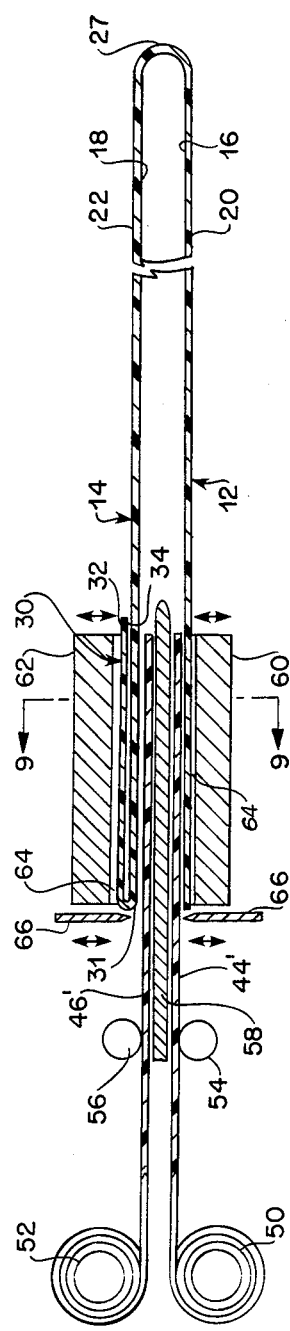
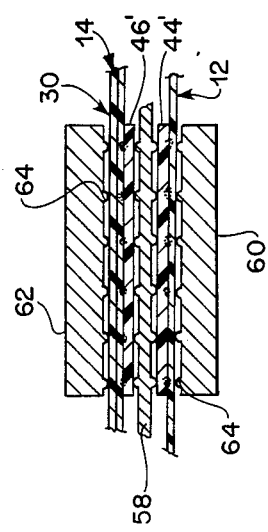
FIG. 8
FIG. 9

BAG WITH CLOSEABLE FLAP AND METHOD OF MANUFACTURING SAME

FIELD OF THE INVENTION

The present invention relates to plastic bags for carrying various types of merchandise, and to a method of manufacturing same. In particular, it relates to a new form of plastic bag which utilizes properties of packaging materials which were previously considered to be undesirable in an unusual and advantageous way to create a particularly convenient and useful package. Still more particularly, it relates to a bag having a closeable flap portion, in which the flap portion, prior to use, is held in position against an outer surface of the bag so as to be stowed in a convenient and accessible manner, thus facilitating manufacturing, shipping and handling.

BACKGROUND OF THE INVENTION

The plastic bag art needs little introduction. Since the advent of inexpensive plastic materials, untold numbers of plastic bags and similar items have been developed and used.

It is simple enough to define the desirable characteristics of a plastic bag. One obviously necessary characteristic is sufficient strength, both in the plastic sheet material itself and in whatever seams may be used to join segments of a bag. It has become extremely popular to create such seams through heat sealing. In this connection, it has become well known that certain plastic materials such as, for example, polyethylene and polypropylene materials, are particularly suitable for forming strong heat seals. Further in this regard, it is also well known to make plastic bag structures having heat sealed seams from laminated sheet materials in which only the mating plies of the sheet materials are of heat sealable material or characteristics (see, for example, U.S. Pat. Nos. 3,456,867; 3,552,638; 4,394,955; and 3,462,070).

Another consideration in the design of a plastic bag is the manner in which it can be decorated with an appealing design or with advertising material, or both. As is well known to those skilled in the art, there are numerous techniques and processes for coating and decorating plastic surfaces. In this regard, it is generally necessary to treat the surfaces of thermoplastic films to render them printable and/or static resistant. Further, it is also known that once plastic surfaces have been so treated or coated in certain manners, it is very difficult—if not impossible—to form a strong heat seal for joining such surfaces. Thus, the nature and manner of the decoration and/or coating are an important consideration in the design of the plastic bags. In particular, it is important to limit the nature of the treatment to areas which are not to be heat sealed during manufacture.

A further consideration in the design of plastic bags is the desire for some form of closing means for the bag opening in order to enclose and protect merchandise in the bag. In this regard, one known closure means comprises a closure flap which may be folded over the bag opening. However, a problem that sometimes arises in connection with closure flaps for plastic bags is the tendency for the closure means to "flap" around loosely, particularly prior to use by a customer, which may hinder the manufacture, the stacking and, eventually, the use of the bags. Thus, in some instances, tape or adhesive have been used to temporarily hold the closure flap in place prior to its use.

A still further desirable characteristic of plastic bags is the provision of a handle to enable the customer or user to conveniently carry his purchase out of the store. Numerous bags have been proposed and used which include a handle member which is normally much stiffer than the remainder of the bag. Handles of this nature are illustrated, for example, in U.S. Pat. Nos. 3,429,498 and 3,693,867. However, such stiff handles add significantly to the cost of manufacturing a bag.

It is also known to make plastic bags with a cutout adjacent the open end which can serve as a handle. However, in such instances, it is necessary to generally provide some type of reinforcement in the handle area, particularly, when the body of the bag is made from very thin sheets of plastic film such as, for example, film of from 1–3 mil thickness. In this regard, it has been proposed to provide double thickness reinforcement in such cutout areas (see, for example, U.S. Pat. No. 3,693,867) or alternatively to extrude the sheet material so as to have a thickened section in the area from which the cutout for the handle opening will be provided. A still further technique which has been employed in the past is to secure a reinforcing patch member to the plastic sheet material in the vicinity of the handle area. Such reinforcing patch members have been secured to the sheet material by means of suitable adhesives and/or by heat sealing techniques.

While many different types of plastic bags and similar items have been developed and used in the prior art, a need still exists for plastic bag structures and methods of manufacture which employ various combinations of desirable features or characteristics, and it is an object of the present invention to provide such a new and improved plastic bag and method of manufacture so as to provide a convenient and useful package and a simplified, efficient and effective method of manufacture.

SUMMARY OF THE INVENTION

In accordance with one aspect of the present invention, there is provided a closeable bag comprised of first and second overlying panel portions each having an inner surface and an outer surface, and which are arranged so that the inner surfaces face one another so as to define an opening between such panel portions. The side edges of the first and second panel portions are sealed along their side edges so as to provide a first seam of a first strength. Additionally, the second panel portion includes a closeable flap portion which extends from and is integral to the second panel portion along a fold line adjacent to the bag opening. The flap portion is initially folded onto the outer surface of the second panel portion and is adapted to be folded about the fold line to close the opening. The flap portion initially is sealed to the outer surface of the second panel portion along the side edges thereof to provide a second seam of a second strength which is weaker than the first strength. The end of the flap portion remote from the fold line is adapted to be pulled away from the outer surface of the second panel portion to break the second seam while the first seam is maintained.

In this manner, a convenient and useful closeable bag is provided in which the closeable flap portion is initially held in position against the outer surface of the bag so as to be stowed out of the way, thus facilitating manufacture, shipping and handling. At the same time, the flap portion may be easily placed in use by breaking the weak side seams holding it in place, without damaging the first seam sealing the side edges of the two panel portions together. Conveniently, in accordance with a preferred embodiment, the outer surfaces of the second panel portion and of the flap portion at at least the side edges have surface characteristics rendering them capable of being only weakly heat sealed together, while the inner surfaces of the first and second panel portions at at least the side edges have surface characteristics rendering them capable of being firmly heat sealed together. Consequently, applying heat and pressure to the overlying stacked side edges of the first and second panel portions and of the flap portion result in a weakened seam between the flap portion and the outer surface of the second panel portion, while a firm, strong heat sealed seram is provided between the inner surfaces of the first and second panel portions along the sides edges thereof. The surface characteristics rendering the outer surfaces capable of being only weakly heat sealed together may conveniently be provided by the introduction of a barrier material therealong, such as, for example, a printing ink used to decorate and/or coat the outer surfaces of the sheet material from which the bag is formed.

In accordance with another aspect of the present invention, there is provided a method of manufacturing a bag in which first and second panel portions of plastic material are provided, each of the panel portions having an inner surface and an outer surface with the inner surfaces, at at least the side edges thereof, having surface characteristics rendering them capable of being firmly heat sealed together. The second panel portion includes an integral flap portion adapted to be folded along a fold line, and the outer surfaces of the second panel portion and of the flap portion at at least the side edges thereof have surface characteristics rendering them capable of being only weakly heat sealed together. In accordance with this aspect of the present invention, the first and second panel portions are positioned in overlying relationship such that the inner surfaces thereof are adjacent to and face one another and such that the side edges thereof are in stacked relationship. The flap portion of the second panel portion is arranged in an initial folded position in which the outer surface of the flap portion is adjacent to and faces the outer surface of the second panel portion and in which the side edges of the flap portion are in stacked relationship to the stacked side edges of the first and second panel portions. The stacked side edges of the first and second panel portions and of the flap portion are then heat sealed together, whereby the side edges of the first and second panel portions are firmly heat sealed together and the side edges of the flap portion are only weakly heat sealed to the second panel portion.

In this manner, a closeable flap will be provided which is initially held in position against the outer surface of the bag and which, when it is desired to use the closeable flap, may be easily separated therefrom without damaging the firm heat seal between the inner surfaces at the side edges of the first and second panel portions. Conveniently, in accordance with a preferred embodiment, the stacked side edges of the first and second panel portions and of the flap portion are heat sealed in a single operation by applying heat and pressure through sealing members arranged on opposite sides of the stacked arrangement of side edges.

In accordance with a still further aspect of the present invention, there is provided a method of manufacturing a bag having a reinforced patch section and a closeable flap portion, which again comprises the steps of providing first and second panel portions of plastic material each of which has an inner surface and an outer surface, and in which the second panel portion includes an integral flap portion adapted to be folded along a fold line. The first and second panel portions are arranged in overlying relationship with the inner surfaces facing one another to define a bag member having an opening along one edge, and such that the fold line about which the flap portion is adapted to fold is adjacent to the one edge. The inner surface of the second panel portion at a predetermined section relative to the one edge has surface characteristics rendering it capable of being firmly heat sealed to a heat sealable material, and the outer surfaces of the second panel portion at the predetermined section and of the flap portion at a predetermined corresponding section relative to the fold line have surface characteristics rendering them capable of being firmly heat sealed together. The flap portion of the second panel portion is initially arranged in a folded position in which the outer surface of the flap portion is adjacent to and faces the outer surface of the second panel portion and in which the predetermined corresponding section of the flap portion overlies the predetermined section of the second panel portion. A reinforcing patch member of heat sealable material is provided for reinforcing the predetermined section of the second panel portion. The reinforcing patch member is arranged in stacked relationship to the overlying predetermined sections of the flap portion and the second panel portion to provide a stacked arrangement in which the patch member is adjacent to and faces the inner surface of the predetermined section of the second panel portion and in which the second panel portion is between the patch member and the flap portion. The patch member is heat sealed to the inner surface at the predetermined section of the second panel portion by applying heat and pressure to sealing members arranged on opposite sides of the stacked arrangement, whereby the patch member is firmly heat sealed to the predetermined section of the second panel portion, with the flap portion not being firmly sealed to the outer surface of the second panel portion. In particular, the flap portion will not be sealed to the outer surface of the second panel portion or will only be lightly bonded thereto.

Thus, in accordance with this aspect of the present invention, the surface characteristics of the outer surface of the second panel portion and the flap portion, which render the outer surfaces incapable of being firmly heat sealed together, are utilized to advantage in order to permit the reinforcing patch to be firmly heat sealed to the inner surface of the second panel portion while preventing the flap and second panel portions from being sealed to one another at the location of the patch member. In this regard, by virtue of the surface characteristics of the outer surface of the second panel portion and the flap portion, the flap portion may be folded back onto the outer surface of the second panel portion during manufacture, with the heat and pressure being applied through sealing members arranged on opposite sides of the stacked arrangement to firmly heat seal the patch to the second panel without causing the flap to likewise be firmly sealed to the second panel portion.

Accordingly, it will be appreciated that in accordance with the various aspects of the present invention, an improved bag having a closeable flap portion and a method of manufacturing same, are provided which utilize properties of packaging materials which were previously considered to be undesirable in an unusual and advantageous way to create a particularly convenient and useful package.

These and further features and characteristics of the present invention will be apparent from the following detailed description in which reference is made to the enclosed drawings which illustrate a preferred embodiment of the present invention.

BRIEF DESCRIPTION OF THE DRAWINGS

FIG. 1 is a plan view of the bag in accordance with the present invention, in which the closeable flap portion is shown in an initial stowed position.

FIG. 2 is a side sectional view taken along line 2—2 of FIG. 1, and substantially enlarged, showing the relationship between the panels and the closeable flap along the side edges, with the firm and weak heat seals being shown schematically.

FIG. 3 is a side sectional view taken along line 3—3 of FIG. 1, and substantially enlarged, showing the relationship between the first and second panel portions, the closeable flap portion and the reinforcing patch members in the handle area.

FIGS. 4 and 5 are a side elevational view and a perspective view, respectively, of the bag of the present invention, illustrating the movement of the closeable flap portion from its initial stowed position towards the closed bag position.

FIGS. 6 and 7 are a side elevational view and a perspective view, respectivley, of the bag of the present invention, illustrating the closeable flap positioned in the closed bag position.

FIG. 8 is a schematic sectional view illustrating how the patch members are secured to the inner surfaces of the first and second panels of the bag of the present invention.

FIG. 9 is a schematic sectional view taken along line 9—9 of FIG. 8.

DETAILED DESCRIPTION OF THE PREFERRED EMBODIMENT

Referring now to the drawings wherein like reference characters represent like elements, there is shown in FIGS. 1-3 a bag member, indicated generally at 10, constructed in accordance with the teachings of the present invention. More particularly, the bag 10 is comprised of first and second panel portions 12, 14 of plastic sheet material each of which has an inner surface 16, 18, respectively, and an outer surface 20, 22, respectively. The panels 12, 14 are arranged in overlying relationship with the respective inner surfaces facing one another, and sealed along the side edges 24, 26 thereof. As is well known, the bottom edge 27 of the bag member 10 is seamed or sealed to thereby provide an enclosure for articles to be packaged or stored therein, and an opening 28 into the interior of the bag 10 is provided along the opposing or top edge. As is conventional, the first and second panel portions 12, 14 may comprise segments of a common sheet of plastic film material which has been folded in half and transversely cut and seamed at spaced intervals to define the sealed side edges 24, 26 of the bag 10, with the bottom seam 22 being provided by the fold in the sheet. Alternatively, the first and second panel portions 12, 14 may comprise separate sheets of a plastic film material which are then seamed along the side 24, 26 and bottom edges 27 in a suitable manner. Although not shown, gussets or folds may be provided along the bottom and/or sides of the bag 10 to allow for expansion of the bag 10 to accomodate various types of merchandise.

In accordance with the present invention, the second panel portion 14 is of a length greater than the first panel portion 12 so that there is provided an extended integral flap portion 30 which is adapted to be folded about a fold line 31 adjacent the opening 28 so as to be capable of closing the opening 28 to protect any articles or materials placed therein. Given the small thickness of the plastic film and its flexibility, it will be appreciated that the fold line 31 may be quite small and unobtrusive, and that the flap portion 30 may be readily folded thereabout. Since the flap portion 30 is actually an extension of the second panel portion 14, its inner and outer surfaces 32, 34, respectively, will be designated "inner" and "outer" consistently with the designation of the surfaces 18, 22 of the second panel portion 14. During manufacture, and prior to use, the foldable flap 30 is positioned so that its outer surface 34 is arranged adjacent to and faces the outer surface 22 of the second panel portion 14 (see FIGS. 1, 2, and 3). However, it will also be appreciated that the flap portion 30 may be lifted from this initial position and folded about the fold line 31 to close the opening 28 between the first and second panel portions 12, 14. As is also shown in FIGS. 1, 2 and 3, portions of the first and second panel portions 12, 14 and of the flap portion 30 are cut out and removed adjacent to the opening 28 to define a handle opening 36 by which the bag 10 may be conveniently carried by a user.

Preferably, the side seams 24, 26 securing together the first and second panel portions, 12, 14 of the bag 10 comprise heat sealed seams formed in a conventional manner through the application of heat and pressure against opposite sides of the panels 12, 14 along the side edges 24, 26. More particularly, the plastic film from which the first and second panels 12, 14 are formed comprises a film of heat sealable material such as, for example, a polyethelene film. The inner surfaces of such films are normally untreated and relatively smooth so as to have a texture and surface characteristics such that they are capable of being heat sealed with conventional heat sealing equipment to a like or similar surface. For purposes of the present invention, it is only necessary that selected portions, for example, along the outer side edges 24, 26 (i.e. the left-hand and right-hand edges as viewed in FIG. 1) and the area of the handle opening 36, have such surface characteristics, although in practice it is anticipated that the entire inner surfaces 16, 18 of the first and second panels 12, 14 will have such surface characteristics. In this regard, in accordance with the preferred embodiment, the first and second panel portions 12, 14 comprise polyethelene sheet material of the type conventionally used in connection with the formation of plastic carrying bags or the like, and thus the entire inner surfaces 16, 18 are of a heat sealable nature. As is well known, such films have a thickness which typically ranges from 1-3 mils, although the thickness may be 10 mils or thicker depending upon the nature of the material and the purposes to which the bag 10 is to be placed.

In accordance with the present invention, the outer surfaces 22, 34 of at least the second panel portion 14 and the flap portion 30, at at least the side edges thereof, have surface characteristics which render them capable of being only weakly heat sealable. More particularly, in contrast to the inner surfaces 16, 18 of the first and second panel portions 12, 14 described previously, the outer surfaces 22, 34 of the second panel portion 14 and the flap portion 30 have a substantially different surface texture and heat sealable characteristic such that, with the use of conventional heat sealing techniques and equipment, only a weak seal would be formed between such outer surfaces 22, 34 and a like surface. Specifically, the quality of the seal formed would be such that it would be unsatisfactory for purposes of joining, for example, the first and second panels 12, 14 of the bag 10 together. However, the weak seal would preferably be strong enough to hold or lightly bond the two components together during certain shipping and handling procedures. Here is should be noted that the strong seal provided between the inner surfaces 16, 18 of the panels 12, 14 with the use of conventional heat sealing techniques and equipment has a strength which typically is substantially equivalent to the strength of the plastic film itself, i.e. during heat sealing the inner surfaces 16, 18 of the panels 12, 14 are fused or welded together.

The outer surface characteristics of the second panel 14 and flap portion 30 for preventing formation of a firm heat seal may be provided in any known manner. For instance, any surface treatment of polyethelene film or the like which introduces a barrier material thereon, such as a printing ink or a coating of varnish, will serve to prevent the formation of firm heat seals if such a surface is attempted to be heat sealed to a like surface or even to an untreated surface. Another technique for providing the desired outer surface characteristics is to provide a laminated sheet material in which the outer ply is of a non-heat sealable material. Also, it is known that most surface treatments of thermoplastic films for rendering them printable, dyeable, static resistant and the like, will have the effect of reducing the strength of the bond formed with the use of conventional heat sealing techniques and equipment. For instance, in order to decorate the surface of a plastic film with an appealing design or advertising material or both, it is generally necessary to electrostatically treat the film, which has the effect of roughing the surface so as to provide for adherence of the printing ink or like material thereto. In this regard, it is known that the strongest weld or seam is achieved with thermoplastic materials when the surfaces being welded together are untreated, and that a very weak seal or bonding is provided when two such electrostatically treated surfaces are attempted to be heat sealed by the application of heat and pressure. A weld or seam of intermediate strength is provided when an untreated surface is attempted to be bonded or fused to an electrostatically treated surface.

Thus, it will be appreciated that in connection with the manufacture of plastic bags from thermoplastic films utilizing the principles of heat sealing to accomplish seaming and welding of segments of the bags together, the decoration of a surface of the film with designs or advertising material or the like can generally introduce complications into the manufacturing process since it is necessary, in order to obtain firm bonding and sealing of the seams, that the areas to be seamed or bonded remain untreated and with no barrier material introduced therebetween. Generally, such complications are avoided in the prior art by confining the treatment and decoration to the outer surfaces 20, 22 of the panels 12, 14 forming the bag 10.

In accordance with the present invention, in which a closeable flap 30 is provided for a bag 10, the inventor has utilized the properties of treated surfaces, previously considered to be undesirable in connection with sealing of the seams, in an unusual and advantageous way to create a particularly unique and useful package or bag 10. Specifically, the inner surfaces 16, 18 of the first and second panel portions 12, 14 may remain untreated so as to have surface characteristics which render them capable of being firmly bonded to a like material, as in the prior art, while the outer surfaces 20, 22, 34, and particularly the side edges of the second panel 14 and the flap portion 30, are treated or provided so as to have surface characteristics which render them incapable of being firmly bonded or sealed together. In other words, the treated outer surfaces 20, 22, 34 are to be used to advantage in connection with manufacture of the bag 10 of the present invention.

More particularly, the outer surfaces 20, 22, 34 of the first and second panels 12, 14 and flap portion 30 are treated such as by electrostatic treatment, printing or applying clear varnish prior to the final manufacture of the bag. The first and second panels 12, 14 are arranged in overlying relationship with the inner surfaces 16, 18 facing one another, either by folding of a single sheet of plastic film or by arranging two separate sheets in overlying relationship. Also, the closeable flap portion 30 of the second panel portion 14 is folded over so as to be adjacent to and face the outer surface 22 of the second panel portion 14 so that a stacked arrangement is provided comprised of the folded flap portion 30, the second panel portion 14 and the first panel portion 12, as illustrated best in FIG. 2. The inner surfaces 16, 18 of the first and second panel portions 12, 14, at the side edges 24, 26 thereof, are then heat sealed together by the application of heat and pressure, in a conventional manner, through the use of sealing members (not shown) arranged on opposite sides of the stacked arrangement. In other words, heat and pressure is applied by a pair of sealing members which contact the outermost surfaces of the stacked arrangement along the side edges 24, 26, i.e. the outer surface 20 of the first panel portion 12 and the inner surface 32 of the flap portion. This operation results in a firm heat seal being formed between the inner surfaces 16, 18 of the first and second panel portions 12, 14, as indicated at 38 in FIG. 2, and in only a weak seal being formed between the outer surface 34 of the flap portion 30 and the outer surface 22 of the second panel portion 14, as indicated at 14 in FIG. 2. That is, because the outer surfaces 22, 34 of the second panel portion 14 and flap portion 30 have surface characteristics rendering them incapable of being firmly heat sealed or bonded together, only a weak seal 40 of a weak or light bonding strength is formed between the flap portion 30 and the outer surface 22 of the second panel portion 14 adjacent the side edges 24, 26.

The firm or strong seal 38 provided between the inner surfaces 16, 18 of the first and second panel portions 12, 14 along the side edges 24, 26 forms the desired seam or weld to maintain the integrity of the bag 10. The weak or light bond 40 formed along the side edges 24, 26 between the flap 30 and the outer surface 22 of the second panel 14 advantageously holds the closeable flap 30 in an initial stowed position such that it will not flap around loosely, which might otherwise hinder the manufacture, stacking or use of the bags 10. In other words, the flap portion 30 is initially held in place out of the way and in an aesthetic manner. Then, when it is desired to use the flap 30 to enclose and protect merchandise placed in the bag 10, the light bond 40 between the flap portion 30 and the outer surface 22 of the second panel 14 may be easily broken without destroying the integrity of the firm bond 38 between the inner surfaces 16, 18 of the first and second panels 12, 14. This latter operation, for example, is shown with reference to FIGS. 5-8 which illustrate the flap portion 30 being ripped or zipped from its initial folded and held position, and then folded over to close the opening 28 betwen the first and second panels 12, 14. In this regard, the inner surface 32 of the flap portion 30 (i.e. the surface facing away from the outer surface 22 of the second panel 14 when the flap 30 is in its initial position) is provided with pressure sensitive strips of tape 42 which can advantageously be used to hold the flap 30 in its closed position as shown in FIGS. 7 and 8.

In many instances, it is desirable to provide suitable reinforcement in the vicinity of the handle opening 36 which is punched through the various sections of the first and second panels 12, 14 and foldable flap 30. In this regard, the punching of an opening through the panel portions 12, 14 which is to be gripped and held by the user presents an area of weakness which may cause the panels 12, 14 to rip or tear when merchandise is placed into the bag 10 and the bag 10 is then carried, particularly when very thin plastic films are used. Thus, oftentimes, particularly with very thin 1-3 mil thick polyethelene bags, reinforcing patch members 44, 46 are secured to the inner surfaces 16, 18 of the first and second panels 12, 14 in the vicinity of the handle opening 36 prior to punching of the handle opening 36 therethrough (see FIGS. 1 and 3). The patch members 44, 46 are of sufficient strength and thickness so as to strengthen the bag material in the handle area, for instance on the order of 5-7 mils thick. The patch members 44, 46 are typically secured to the inner surfaces 16, 18 by means of heat sealing or through the use of an adhesive, although adhesives generally require additional types of equipment and techniques.

In the conventional manufacture of bags having patch members in which, the patch members are secured to the inner surfaces by heat sealing, a central support bar or plate is arranged between the overlying first and second panel portions, and the patch members introduced along opposite sides of the central plate so as to be adjacent the inner surface of the first and second panel portions at the desired location. The patch members are then heat sealed to the respective inner surfaces through the application of heat and pressure by means of sealing members, such as heater bars, which contact the outer surface of the respective panels and press against the centrally disposed support plate. After the patches are heat sealed in place, the handle opening is cut therethrough. When the bags are formed from a continuous sheet or sheets of plastic film, the patch introduction and securing station is located upstream of the edge seaming station.

Previously, it was not thought possible to employ such a procedure for securing reinforcing patch members 44, 46 in connection with a foldable closure flap 30 as the flap 30 would interfere with insertion of the patch members 44, 46 if it were to extend beyond the edge of the first and second panels 12, 14 or would itself be fused to one of the panel portions 12, 14 if it were folded out of the way. However, with the present invention, employment of a foldable flap portion 30 in the manner as previously described, in which the surface characteristics of the outer surfaces 22, 34 of the flap 30 and second panel are treated so as to not be firmly heat sealable to one another, will allow for the patch members 44, 46 to be heat sealed to the inner surfaces 16, 18 without also sealing the flap portion 30 against the outer surface 22 of the second panel 14 at the location at which the patch members contact the panel 14.

More particularly, a schematic illustration of the operation in accordance with the present invention for securing the patch members 44, 46 to the inner surfaces 16, 18 of the panels 12, 14 of a bag 10 is shown in FIGS. 8 and 9. As illustrated there, the bag 10 is formed from a single web of sheet material folded in half to define first and second panels 12, 14, with the second panel 14 having an extended end folded back onto itself to provide the flap portion 30. The web of plastic film is moved intermittently in a direction into the paper as shown in FIG. 8 (or to the right as shown in FIG. 9). Arranged transversely to one side of the path of movement of the web, there is provided a pair of supply rolls 50, 52 of suitable plastic sheet material from which the reinforcement patches 44, 46 are to be formed, the strips of reinforcing patch material 44', 46' being directed via feed or drive rolls 54, 56 onto opposite sides of a central support plate 58 arranged between the first and second panel portions 12, 14 adjacent the open end 28 thereof. The operation of the feed rolls 54, 56 is controlled such that the free ends of the patch sheet materials 44', 46' are introduced a specified distance into the space betwen the first and second panels 12. 14.

After the free ends of the patch sheet materials 44', 46' have been moved into the proper position and the web has stopped its travel, a pair of sealing members 60, 62 arranged below and above the web are moved by suitable means (not shown) toward one another so as to clamp the portions of the patch film 44', 46' between each of the panel portions 12, 14 and the central plate 58. The sealing members 60, 62 apply heat and pressure to the juncture between the respective inner surfaces 16, 18 of the panels 12, 14 and the patch material 44', 46' in contact therewith to thereby weld or fuse the components together. However, because the facing outer surfaces 22, 34 of the second panel 14 and flap 30 have been treated or provided so as to be incapable of forming a strong heat seal, the flap portion 30 will not be sealed to the outer surface 22 of the second panel 14 at the location of the patches 44, 46. As is known in connection with conventional patch sealing operations, the sealing members 60, 62 may have raised lands 64 (see FIG. 9) which are at the desired heat sealing temperature so as to heat seal the patches 44, 46 to the respective inner surfaces 16, 18 of the first and second panels 12, 14 in a series of spaced weld lines. Typically, teflon coated shades (not shown) cover the sealing members 60, 62 so as to assure release of the sealing members 60, 62 from the web after the heat sealing operation is complete. While the sealing members 60, 62 are in contact with the web, applying heat and pressure, knife members 66 may be moved to cut the patch members 44, 46 from their respective webs, to thereby allow the panel portions 12, 14 to be moved to the next operation. In this regard, the next operation comprises a cutting operation in which the handle opening 36 is punched through the flap portion 30, the first and second panel portions 12, 14 and the heat sealed patches 44, 46. The next operation thereafter typically comprises the edge seaming operation.

The heat sealing technique employed for sealing the patch members 44, 46 in accordance with the preferred embodiment of the present invention is what is conventionally known as a bottom or pressure seal in which the heat, pressure and dwell time of the equipment is controlled precisely in order to fuse the patch members 44, 46 to the inner surfaces 16, 18 of the respective panels 12, 14 without creating a burn-through condition. In this regard, while the application of heat and pressure in accordance with the present invention does not create any firm seal between the flap portion 30 and the outer surface 22 of the second panel 14 in the vicinity of the patch 46, the flap portion 30 does act as an insulator to the passage of heat and thus a slightly higher temperature should be employed for the upper sealing member 62 in order to assure that adequate heat reaches the juncture between the patch 46 and the inner surface 18 of the second panel 14. However, the amount of increase in temperature is not significant, and adjustment of the temperature employed to accomodate different materials, different thicknesses of materials, etc. is well within the ordinary skill of artisans familiar with heat sealing operations and equipment. Typically, the sealing members 60, 62 are at a temperature on the order of between 350°–550° F., depending upon the speed and thickness of the film. As the sealing members 60, 62 generally include a teflon shade over the lands 64 for insuring proper release properties such that the web does not adhere to the sealing members 60, 62, the temperature of the sealing members 60, 62 should not exceed about 550° F. as otherwise the release properties of the shade would be destroyed.

The side weld seams 24, 26 for sealing the inner surfaces 16, 18 of panels 12, 14 of a burn-through seal technique which relies principally on a heated knife which is at a sufficient temperature to burn through the sheet material while simultaneously sealing the side edges. Typically, the knife edge for forming the side weld seams 24, 26 is at a temperature on the order of 700°–1,000° F., and is pressed against an opposing support member with the first and second panels 12, 14 therebetween. At this temperature, the necessary heat is applied for causing the plastic material to be cut or severed, with the edges of the inner surfaces 16, 18 of the first and second panels 12, 14 being firmly heat sealed together substantially simultaneously. However, the flap portion 30 will only be lightly bonded to the outer surface 22 of the second panel 14, as discussed above. As is known in the art, a temperature of less than about 500° F. will be insufficient to create a cut and seal as is necessary for formation of the bag 10.

The strength of the light bond 40 between the flap portion 30 and the outer surface 22 of the second panel portion 14 should be sufficient to hold the flap 30 in place, while at the same time allowing the flap 30 to be capable of being easily ripped or zipped away from the outer surface 22 without damaging whatsoever the firm seal 38 formed between the inner surfaces 16, 18 of the first and second panels 12, 14. In this regard, it will be appreciated that the side edge seams 24, 26 are formed with a hot knife which essentially burns through the polyethelene because of the high temperature of the knife edge. This has the effect in some instances of creating a small "rollover" effect in connection with the melting or fusing of the inner surfaces 16, 18 of the first and second panel portions 12, 14, which advantageously aids in lightly bonding the flap portion 30 to the outer surface 32 of the second panel 14. On the other hand, because the temperature of the sealing members 60, 62 for securing the patches 44, 46 is generally much lower, in essence, no light bonding will occur in the area at which the patch member 46 is secured by virtue of the surface characteristics of the outer surface 22 of the second panel portion 14. However, it will be appreciated that in some instances it may be desirable to provide a light bond thereat in order to aid in the holding of the flap portion 30 in place, which could, for example, be provided by use of a heated knife edge in connection with cutting the handle opening 36, and/or increasing the heat, pressure and/or a dwell time of the sealing member 62.

Thus, in essence, the firm bond or heat seal 38 between the inner surfaces 16, 18 of the first and second panels 12, 14 along the side edges 24, 26, or between the patch member 44, 46 and the inner surfaces 16, 18 of the panels 12, 14 in the patch area, is of a strength which substantially approaches the strength of the plastic material itself, whereas the light bond 40 produced in accordance with the present invention is of significantly less strength and, in some instances, may even approach, as in the patch area, substantially no strength at all.

The types of materials with which the present invention may be utilized may comprise any of the typical thermoplastic films which are well known to be of a heat sealable nature. The most well known of such films include films of polyethelene, polypropylene and in some instances, vinyl. As for the nature of the treatment for rendering portions of the outer surfaces 22, 34 of the second panel 14 and flap 30 incapable of forming a strong or firm bond, this may be accomplished by applying to the surface of a heat sealable film a coating of any material which will create or form a barrier. Such barrier materials, for example, may include ink for decorating the film surface, a clear varnish, or virtually any nonpolyethelene-based material. Further, the surface of a heat sealable film could be treated electrostatically. As is known, two such electrostatically treated surfaces, when conventional heat sealing equipment is employed, will only produce a slight tack and not a strong seal, whereas a seal of intermediate strength is provided when an electrostatically treated surface is adhered to an untreated surface conventional heat sealing equipment. On the other hand, in order to produce a firm bond or seal, both surfaces must be untreated. Still further, a non-heat sealable material could be laminated to a heat sealable film to thereby provide surface characteristics incapable of rendering a strong bond.

Also, while the heat sealing techniques and equipment employed in accordance with the preferred embodiment of the present invention the use of heated members, it will be appreciated that other types of means or tools for creating heat seals, such as, for example, ultrasonic equipment, could be employed, especially for use in connection with heavy gauge films or vinyl type materials.

Accordingly, it will be appreciated that in accordance with the present invention there is provided a closeable bag 10 comprised of first and second overlying panel portions 12, 14 each having an inner surface 16, 18 respectively and an outer surface 20, 22 respectively, the inner surfaces 16, 18 of the panel portions 12, 14 being sealed along the side edges 24, 26 thereof to provide a first seam 38 of a first strength and to define an opening 28 between the first and second panel portions 12, 14. A flap portion 30 extends from and is integral to the second panel portion 14, the flap portion 30 being adapted to be folded along a fold line 31 adjacent the opening 28 and initially positioned so as to be folded onto the outer surface 22 of the second panel portion 14. The flap portion 30 is initially sealed to the outer surface 22 of the second panel portion 14 along the side edges 24, 26 thereof so as to provide a second seam 40 of a second strength which is weaker than the first strength, and the end of the flap portion 30 remote from the fold line 31 is adapted to be pulled away from the outer surface 22 of the second panel portion 14 to break the second seam 40 while the first seam 38 is maintained.

According to a further aspect of the present invention, there is provided a method of manufacturing a bag 10 in which the inner surfaces 16, 18 of first and second panel portions 12, 14 at at least the side edges 24, 26 thereof have surface characteristics rendering them capable of being firmly heat sealed together and in which the outer surfaces 22, 34 of the second panel portion 14 and an extended flap portion 30 at at least the side edges 24, 26 thereof have surface characteristics rendering them capable of being only weakly heat sealed together. In accordance with this aspect of the invention, the first and second panel portions 12, 14 are arranged in overlying relationship such that the inner surfaces 16, 18 thereof are adjacent to and face one another, and with the side edges 24, 26 thereof in stacked relationship, and the flap portion 30 is arranged in an initial folded position so that the outer surface 34 of the flap portion 30 is adjacent to and faces the outer surface 22 of the second panel portion 14 and so that the sides edges 24, 26 of the flap portion 30 are in stacked relationship to the side edges 24, 26 of the first and second panel portions 12, 14. The stacked side edges 24, 26 of the first and second panel portions 12, 14 and the flap portion 30 are then heat sealed together whereby the side edges 24, 26 of the first and second panel portions 12, 14 are firmly heat sealed together and the side edges 24, 26 of the flap portion 30 are weakly heat sealed to the second panel portion 14.

According to still a further aspect of the present invention, there is provided a method of manufacturing a bag 10 having a reinforced patch section 46 and closeable flap portion 30, in which first and second panel portions 12, 14 of plastic material are provided and arranged in overlying relationship so that the inner surfaces 16, 18 thereof face one another to define a bag member 10 having an opening 28 along one edge. The second panel portion 14 includes an integral flap portion 30 that is adapted to be folded along a fold line 31 adjacent to the one edge for closing the opening 28 of the bag member 10. The inner surface 18 of the second panel portion 14 at a predetermined section relative to the one edge has surface characteristics rendering it capable of being firmly heat sealed to a heat sealed material, and the outer surface 22 of the second panel portion 14 at the predetermined section and of the flap portion 30 at a predetermined corresponding section relative to the fold line 31 have surface characteristics rendering them incapable of being firmly heat sealed together. The flap portion 30 is initially arranged in a folded position in which the outer surface 34 of the flap portion 30 is adjacent to and faces the outer surface 22 of the second panel portion 14 and in which the predetermined corresponding section of the flap portion 30 overlies the predetermined section of the second panel portion 14. A reinforcing patch member 46 of heat sealable material is provided for reinforcing the predetermined section of the second panel portion 14, the reinforcing patch member 46 being arranged in stacked relationship to the overlying predetermined sections of the flap portion 30 and second panel portion 14 to provide a stacked arrangement in which the patch member 46 is adjacent to and faces the inner surface 18 of the predetermined section of the second panel portion 14 and the second panel portion 14 is between the patch member 46 and the flap portion 30. The patch member 46 is heat sealed to the inner surface 18 of the second panel portion 14 by applying heat and pressure to sealing members 60, 62 arranged on opposite sides of the stacked arrangement, whereby the patch member 46 is firmly heat sealed to the predetermined section of the second panel portion 14 and the flap portion 30 is prevented from being firmly sealed to the outer surface 22 of the second panel portion 14.

As will be readily apparent to those skilled in the art, the present invention may be used in other specific forms without departing from its spirit or essential characteristics. The preferred embodiment is therefore to be considered as illustrative and not restrictive, the scope of the invention being indicated by the claims rather than the foregoing description, and all changes which come with the meaning or range of equivalents of the claims are therefore intended to be embraced therein.

What is claimed is:

1. A closeable bag comprising:

first and second overlying panel portions and a flap portion extending from and integral to said second panel portion, said first and second panel portions and said flap portion each having an inner surface and an outer surface, said inner surfaces of said first and second panel portions at at least side edges thereof having surface characteristics which render them capable of being firmly heat sealed together, and said outer surfaces of said second panel portion and said flap portion at at least side edges thereof having surface characteristics which render them capable of being only weakly heat sealed together;

said inner surfaces of said first and second panel portions being heat sealed along said side edges thereof to provide a first heat sealed seam of a first strength and to define an opening between said first and second panel portions;

said flap portion being initially heat sealed to said outer surface of said second panel portion along said side edges thereof to provide a second heat sealed seam of a second strength which is weaker than the first strength, said second heat sealed seam along said side edges of said flap portion and said second panel portion overlying said first heat sealed seam along said side edges of said first and second panel portions, and the end of said flap portion remote from said fold line being adapted to be pulled away from said outer surface of said panel portion to break said second heat sealed seam while said first heat sealed seam is maintained so that said flap portion may be folded about said fold line to close said opening.

2. The closeable bag of claim 1 wherein said outer surfaces are electrostatically treated.

3. The closeable bag of claim 1 wherein said outer surfaces are coated with a material which prevents said surfaces from being firmly heat sealed together.

4. The closeable bag of claim 3 wherein said outer surfaces are coated with an ink.

5. The closeable bag of claim 3 wherein said outer surfaces are coated with a varnish.

6. The closeable bag of claim 1 wherein said first and second panel portions at predetermined sections relative to said opening include reinforcing patch members secured to said inner surfaces of said first and second panel portions.

7. The closeable bag of claim 6 wherein said patch members are heat sealed to said inner surfaces of said first and second panel portions.

8. The closeable bag of claim 6 wherein further including a handle opening extending through said patch members and said first and second panel portions to provide a handle for said bag.

9. The closeable bag of claim 1, further including handle means for providing a handle for said bag.

10. The closeable bag of claim 9 wherein said handle means comprises a handle opening extending through said first and second panel portions adjacent said opening between said first and second panel portions.

11. The closeable bag of claim 10 wherein said handle opening also extends through said flap portion such that said handle opening in said flap portion is aligned with said handle opening in said first and second panel portions when said flap portion is in said initial folded position.

12. The closeable bag of claim 1, further including means for fastening said flap portion to said first panel portion after said second seam is broken and said flap portion is folded about said fold line to close said opening.

13. The closeable bag of claim 1 wherein said first and second panel portions are formed from a continuous sheet of plastic material, and wherein said inner surfaces of said first and second panel portions comprise one of the surfaces of said continuous sheet of plastic material and said outer surfaces of said first and second panel portions comprise the other of the surfaces of said continuous sheet of plastic material.

14. A method of manufacturing a bag, comprising the steps of:
providing first and second panel portions of plastic material, each of said panel portions having an inner surface and an outer surface, said second panel portion including an integral flap portion adapted to be folded along a fold line, said inner surfaces of said first and second panel portions at at least the side edges thereof having surface characteristics rendering them capable of being firmly heat sealed together, and said outer surfaces of said second panel portion and of said flap portion at at least the side edges thereof having surface characteristics rendering them capable of being only weakly heat sealed together;
positioning said first and second panel portions in overlying relationship such that said inner surfaces thereof are adjacent to and face one another and such that the side edges thereof are in stacked overlying relationship;
arranging said flap portion of said second panel portion in an initial folded position in which said outer surface of said flap portion is adjacent to and faces said outer surface of said second panel portion, and in which the side edges of said flap portion are in stacked overlying relationship to the side edges of said first and second panel portions; and
heat sealing together the stacked side edges of said first and second panel portions and said flap portion, whereby said side edges of said first and second panel portions are firmly heat sealed together and said side edges of said flap portion are weakly heat sealed to said second panel portion.

15. The method of manufacturing of claim 14, further including the step of heat sealing reinforcing patch members to said inner surfaces of said first and second panel portions at predetermined sections of said first and second panel portions.

16. The method of claim 14 wherein said first and second panel portions are provided by a single sheet of plastic material.

17. The method of manufacturing of claim 14 wherein said surface characteristics of said outer surfaces of said first and second panel portions are provided by treating said outer surfaces electrostatically.

18. The method of claim 14 wherein said surface characteristics of said outer surfaces of said first and second panel portions are provided by coating said outer surfaces with a material which prevents said surfaces from being heat sealable to a like material.

19. The method of claim 18 wherein said outer surfaces are coated with an ink.

20. The method of claim 18 wherein said outer surfaces are coated with a varnish.

* * * * *